United States Patent [19]

Mann

[11] Patent Number: 4,506,679
[45] Date of Patent: Mar. 26, 1985

[54] ENDOCARDIAL ELECTRODE

[76] Inventor: Alfred E. Mann, 301 S. Cliffwood Ave., Los Angeles, Calif. 90049

[21] Appl. No.: 430,912

[22] Filed: Sep. 30, 1982

[51] Int. Cl.³ .............................................. A61N 1/02
[52] U.S. Cl. .................................... 128/785; 128/786
[58] Field of Search ............................... 128/784–786, 128/419 P

[56] References Cited

U.S. PATENT DOCUMENTS 4,236,529 12/1980 Little .................................... 128/785
4,269,198 5/1981 Stokes ................................. 128/785
4,301,815 11/1981 Doring ................................ 128/785

Primary Examiner—Lee S. Cohen
Attorney, Agent, or Firm—Robert R. Meads

[57] ABSTRACT

An improved endocardial electrode (10) of the type having an electrical conductor (14) encased in material (16) which is generally inert to body fluids and terminating at an exposed, electrically conductive tip (12). A plurality of non-conductive, resilient tines (20) extends from the encasing material (16) near the electrode tip (12). Each tine (20) forms a substantially ninety degree angle with respect to the electrical conductor (14). A blocking surface (22) is provided adjacent to a portion of each tine (20) surface facing the electrode tip (12). The blocking surface (22) allows only an upper portion of each tine to be deformed in the direction of the electrode tip (12) while allowing the entire tine to be deformed away from the electrode tip, thereby providing a decreased deformation resistance as the electrode tip (12) is inserted into a vein (34) or between heart trabeculae, and an increased deformation resistance as the electrode tip (12) is withdrawn through a vein (34) or from heart trabeculae.

23 Claims, 13 Drawing Figures

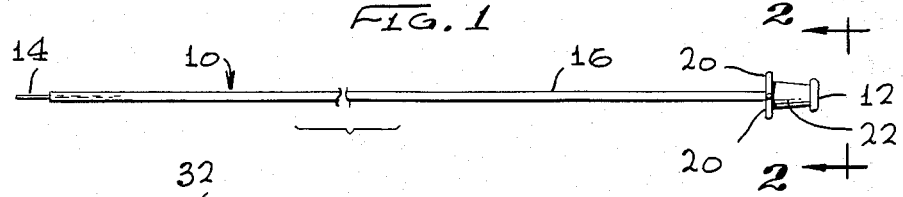
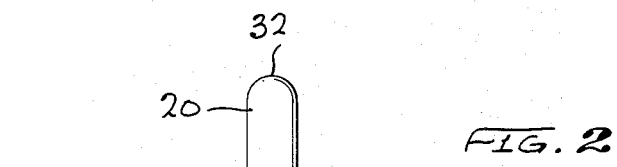
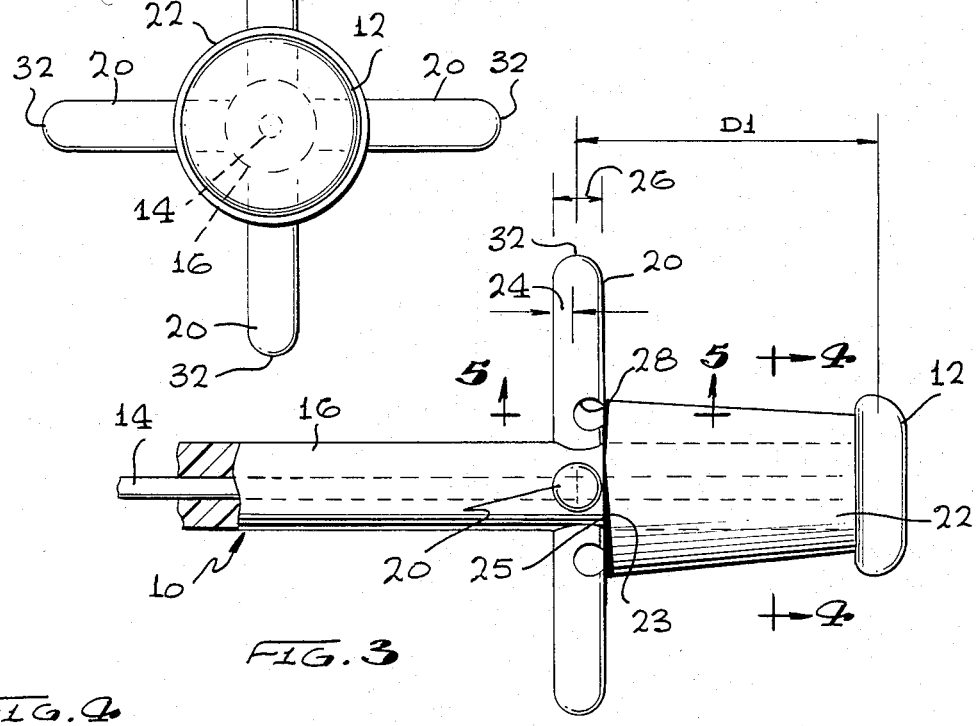
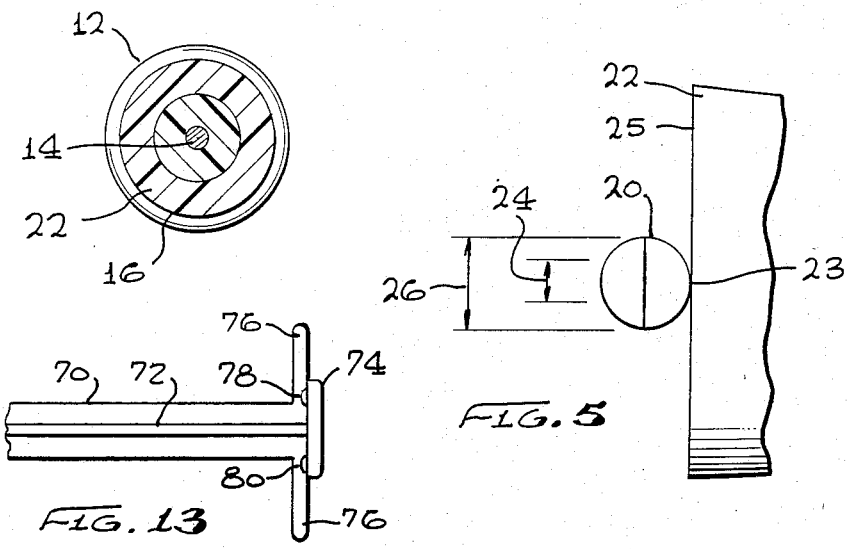

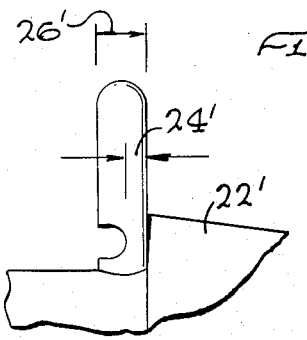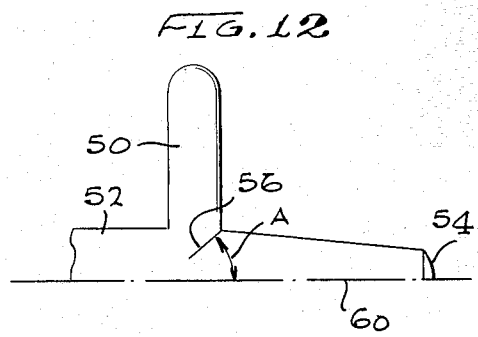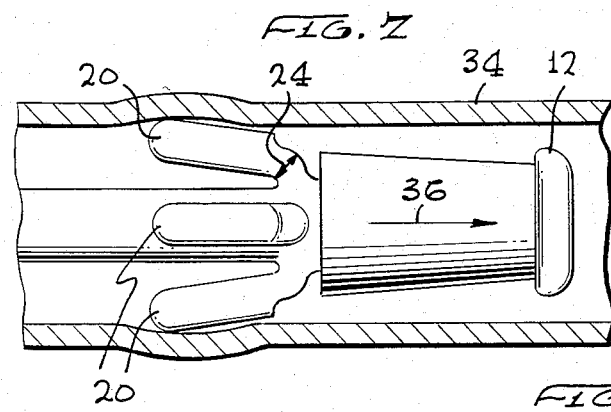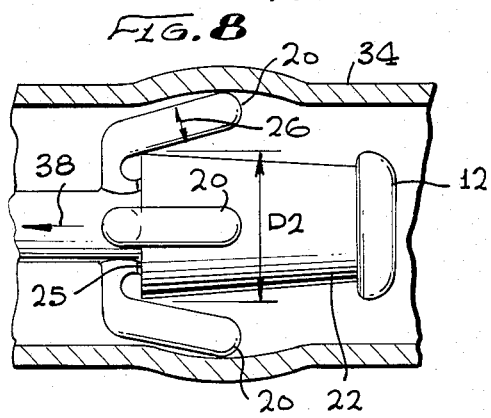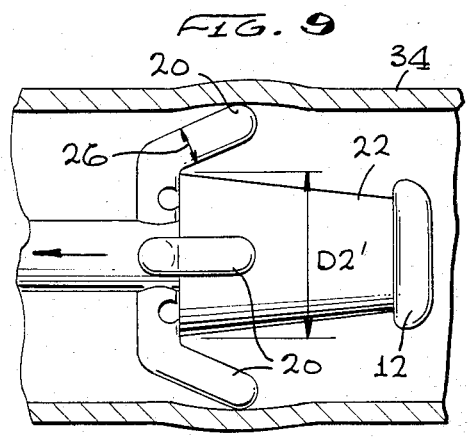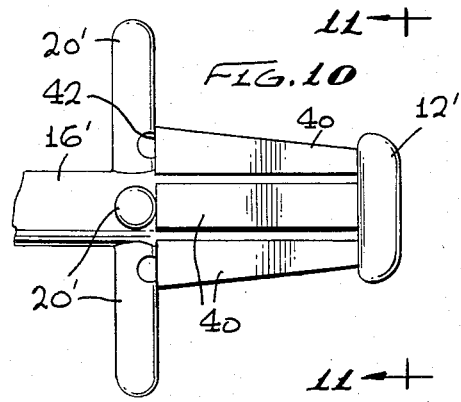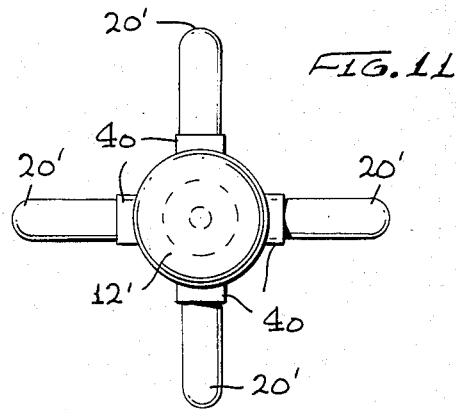

ENDOCARDIAL ELECTRODE

FIELD OF THE INVENTION

The invention relates to medical electrodes, and more particularly to endocardial electrodes having outwardly extending tines located near an electrode tip.

BACKGROUND OF THE INVENTION

Endocardial electrodes include an exposed metallic electrode tip at the end of a tubular insulating sheath, the sheath generally being made of silicone rubber, polyurethane or other insulating material which is generally inert to body fluids. The sheath surrounds an electrically conductive electrode for providing electrical continuity between the electrode tip and the other end which usually terminates in a connector that is removably attached to a pulse generator such as a heart pacemaker. This particular type of electrode is known as a unipolar electrode, the pulse generator case being the other electrode. Another type of electrode is known as a bipolar electrode. It includes two electrically conductive electrodes, one connected to the exposed electrode tip and the other to a second exposed electrode generally in the form of an annular ring near the electrode tip.

Originally, electrode tips did not incorporate a mechanical means for preventing their dislodgement from the heart trabeculae. As endocardial electrodes were improved, a plurality of wedge-shaped protrusions formed of a material substantially inert to body fluids was located immediately behind the electrode tip for engaging the trabeculae and providing some mechanical restraint against tip dislodgement. A number of trabeculae-gripping devices have been utilized, including tines formed out of a plastic or metallic material that are retracted during electrode insertion and then extended to engage the trabeculae. In some configurations the wedges were solid, and in others they were conically shaped and hollow. Some configurations replaced the conical shape by a series of elements of the cone which are referred to as "tines". One configuration has tines extending backwardly from an area immediately behind the tip at an acute angle of approximately forty-five degrees. Such a configuration is described in U.S. Pat. No. 3,902,501 to Citron, et al. Tines differ from closed cones principally in that they are generally more flexible and can be made longer, thus tending to be captured better by the trabeculae. Tines in conventional endocardial electrodes bend toward the cylindrical sheath of the lead during lead insertion, thereby reducing its cross-section. Once the ventrical is entered, the tines expand to an acute angle and engage the trabeculae. However, during insertion of the electrode tip into the trabeculae, the tines are further bent down toward the sheath and compressed. Although the tines occasionally capture one or more of the trabeculae, their inherent resiliency to assume the unrestrained acute angle tends to push the tip out of the area of maximum electrical contact with the heart tissue, thereby acting somewhat as a spring and pushing the electrode tip from its furthest penetration. The endocardial electrode provided by the invention tends to minimize this problem by incorporating tines which provide one resistance when the electrode tip is being pushed into the trabeculae or through a vein, and another resistance when the tip is being withdrawn from the trabeculae or through a vein.

SUMMARY OF THE INVENTION

The invention provides an improved endocardial electrode having an electrical conductor encased in an encasing material which is generally inert to body fluids. The conductor terminates at an exposed electrically conductive electrode tip. The improved endocardial electrode includes a resilient tine means consisting of at least one tine extending from the encasing material near the electrode tip. The tine is characterized by a first deformation resistance when its tip is moved away from the electrode tip. The invention further provides a means for providing a second deformation resistance different from the first deformation resistance when the tine tip is moved towards the electrode tip.

In specific embodiments of the invention, the second deformation resistance is greater than the first deformation resistance. A stop means is provided immediately adjacent to a lower portion of the tine between the tine and the electrode tip, the stop means providing a blocking surface extending upwardly from the encasing material for a predetermined distance. When the tine tip is moved away from the electrode tip, the entire length of the tine can be deformed whereas when the tine tip is moved towards the electrode tip, only the portion of the tine extending above the stop means is allowed to bend towards the electrode tip. Thus, the tine itself offers a greater deformation resistance when its tip is moved towards the electrode tip than when it is moved away from the electrode tip. Embodiments of the stop means disclosed include a truncated cone which is concentrically positioned with respect to the encasing material to provide an annular surface as a stop means. In another embodiment, a plurality of wedges each corresponding to one of the tines is provided, each wedge defining a blocking surface adjacent to a lower portion of its associated tine. Thus, it can be appreciated that the amount of deformation resistance provided by the tine to a predetermined withdrawal force is related to the height of the blocking surface with respect to the length of the tine. The higher the blocking surface extends with respect to the tine length, the more resistance the tine tip offers to being moved in the direction of the electrode tip.

A means is also disclosed for varying the amount of deformation resistance the tine offers as its tip is moved away from the electrode tip. This is effected by decreasing the diameter of a tine portion immediately adjacent to the blocking surface, thereby reducing the deformation resistance when the tine tip is moved away from the electrode tip, while substantially unaffecting the deformation resistance when the tine tip is moved towards the electrode tip.

BRIEF DESCRIPTION OF THE DRAWINGS

FIG. 1 is a plan view of an improved endocardial electrode provided by the invention;

FIG. 2 is a front view of the electrode tip and tines taken along line 2—2 of FIG. 1;

FIG. 3 is a plan view of the end portion of the electrode showing the tines and electrode tip;

FIG. 4 is a cross-sectional view taken along line 4—4 of FIG. 3;

FIG. 5 is a cross-sectional view taken along line 5—5 of FIG. 4;

FIG. 6 is a cross-sectional view showing an alternate tine configuration;

FIG. 7 is a plan view of the end portion of the electrode as it is inserted through a vein;

FIG. 8 is a plan view of the end portion of the electrode as it is withdrawn through a vein;

FIG. 9 is a plan view of the end portion of an electrode as it is withdrawn through a vein, the end portion being configured to provide a greater withdrawal resistance than the end portion of FIG. 8;

FIG. 10 is a plan view of the end portion of an electrode showing a further embodiment of the stop means;

FIG. 11 is an end view taken along line 11—11 of FIG. 10;

FIG. 12 is a plan view showing an alternate embodiment of the invention; and

FIG. 13 is a cross-sectional view of a still further embodiment of an electrode according to the invention.

DETAILED DESCRIPTION

Detailed illustrative embodiments of the invention disclosed herein exemplify the invention and are currently considered to be the best embodiments for such purposes. They are provided by way of illustration and not limitation of the invention. Various modifications thereof will occur to those skilled in the art, and such modifications are within the scope of the claims which define the present invention.

As previously explained, an improved endocardial electrode is disclosed which incorporates four resilient tines spaced at substantially ninety degree increments around an encased, longitudinally-extending central conductor, the tines extending outwardly from the conductor at substantially ninety degree angles when unrestrained. A stop means in the form of a truncated cone is provided between the extended tines and an electrode tip connected to the conductor end. The stop means is positioned so that only a portion of each tine can bend towards the electrode tip whereas the entire tine can bend away from the electrode tip. This configuration provides different insertion and withdrawal forces for the electrode and also results in a more secure positioning of the electrode tip with respect to an inside surface of a user's heart.

Referring now to FIGS. 1 and 2, an improved endocardial electrode 10 is shown having an exposed electrode tip 12 and a central conductor 14 for conducting electrical pulses from a tissue stimulating device such as a heart pacemaker (not shown) to the electrode tip 12. An encasing tube 16 formed of a non-conductive material which is substantially inert to body fluids is provided along the length of the conductor 14 for insulating the conductor 14 from the user's body. This insulating material could be either a polyurethane or silicone rubber for example. Four tines 20 are located near the electrode tip 12, the tines being formed of a deformable resilient material such as a polyurethane or silicone rubber. The tines 20 are placed at substantially ninety degree angles about the central conductor 14, and when unrestrained extend outwardly from the central conductor 14 at substantially ninety degree angles. Although the configuration shown in FIGS. 1 and 2 shows four tines, it should be recognized that any number of tines could be utilized. A restraining wedge 22 in the form of a truncated cone is located between the tines 20 and the electrode tip 12 in order to block or stop a portion of the tines 20 from bending towards the electrode tip 12 while allowing the entire tine 20 to bend away from the electrode tip 12 as will be explained in further detail below.

Referring now to FIG. 3, the tines 20 and restraining wedge 22 can be seen in more detail. The tines 20 are spaced apart from the electrode tip 12 by a distance D1, D1 generally being less than ¼ inch. The restraining wedge 22 is in the shape of a truncated cone having its larger diameter adjacent to the tines 20 and its smaller diameter adjacent to the electrode tip 12. In the particular embodiment disclosed, the restraining wedge 22 has a centrally located bore having an inner diameter equal to the outer diameter of the encasing tube 16. This can be seen in the cross-sectional view of FIG. 4. The diameter of the encasing tube 16 is shown as significantly less than that of the wedge 22 for illustrative purposes. In practice, however, the diameter of the encasing tube should be only slightly smaller than that of the restraining wedge.

In assembly, the encasing tube 16 is positioned within the inner bore of the restraining wedge, the electrode tip 12 then being attached to the central conductor 14 and positioned so that it maintains the restraining wedge 22 in an abutting relationship with respect to the tine surface 23 facing the electrode tip 12. Alternatively, the restraining edge 22 could be formed of the same material as the encasing tube 16 and the tines 20, the entire assembly then being molded as one piece.

Other configurations could also be utilized. For example, the entire group of tines 20 could be formed to extend from a cylindrical tube as a separate part which could then be slid over and concentrically positioned with respect to the encasing tube 16, and then fixed in position mechanically, or by gluing adjacent to the restraining wedge 22, and in an abutting relationship with respect to the tine surface 23 as previously explained. A still further configuration would include the tines 20 and wedge 22 being formed as a separate assembly having a central bore which is adapted to be slidably positioned along the outer surface of the encasing tube 16 and adjacent to the electrode tip 12.

A further feature of the exemplary embodiment provides for altering the deformation resistance of each tine 20 as its tip is moved away from the electrode tip 12 with respect to its deformation resistance as it is moved towards the electrode tip 12. This is effected by configuring each tine 20 so that a weakened portion 24 has a smaller thickness than that of other portions of the tine 20. The weakened portion 24 is located opposite a blocking surface 25 formed by the restraining wedge 22. The blocking surface 25 is substantially orthogonal to the central conductor 14. Referring to FIGS. 3 and 5, one relationship of the weakened portion 24 of the tine 20 with respect to a non-weakened portion 26 and the restraining wedge 22 can be seen. It can be appreciated that when a tip 32 of the tine 20 is moved toward the electrode tip 12, the non-weakened portion 26 of the tine 20 will be deformed. However, when the tine tip 32 is moved away from the electrode tip 12, less force will be required due to the weakened portion 24. Thus, more force is required to move the tip 32 towards the electrode tip 12 than away from the electrode tip 12. The amount of force required to move the tine tip 32 away from the electrode tip 12 is related to the thickness of the weakened portion 24, whereas the force required to move the tip 32 toward the electrode tip 12 is substantially determined by the thickness of the non-weakened portion 26 and the height of the blocking surface 25 with respect to the length of the tine 20 as shown at 28.

Both the forward and backward deformation resistances required to move the tine tip 32 can be readily adjusted by choosing the thickness of the weakened portion 24, the non-weakened portion 26, and the height of the blocking surface 25. The tine 20 could of course have the same thickness along its entire length and still exhibit different deformation resistances as its tip is moved towards and away from the electrode tip 12.

FIG. 6 shows a tine 26' having a weakened portion 24' proximal to the restraining wedge 22' whereas FIG. 5 shows the weakened portion 24 distal from the restraining wedge 22. It should also be noted that the weakend portion need not have a smaller cross-sectional area than the tine itself. For example, it could have an elliptically-shaped cross-sectional area having a minor axis which is perpendicular with respect to the blocking surface 25. Another technique for creating a weakened portion would be to have small cuts or grooves formed in the tine portion proximal to the central conduction and adjacent to the blocking surface, thereby reducing the flex or deformation resistence when the tine tip is moved backwardly with respect to the electrode tip.

Referring now to FIG. 7, a plan view of the tines 20 and electrode tip 12 can be seen when positioned within a vein 34. When the electrode tip 12 is being inserted or pushed through the vein 34 in the direction indicated by the arrow 36, the tines 20 and vein 34 will deform to the configuration essentially as shown. As previously explained, the diameter of the weakened portion 24 basically determines the amount of deformation resistance required to position the tines 20 as shown. However, when the electrode tip 12 is being withdrawn through the vein 34 in a direction indicated by the arrow 38 shown in FIG. 8, the tines 20 will be positioned essentially as shown. Thus, the amount of deformation resistance required to position the tines 20 away from the electrode tip 12 is related to the diameter of the non-weakened portion 26 and the diameter D2 of the blocking surface 25.

FIG. 9 illustrates that as the diameter D2' of the blocking surface is increased, less of the non-weakened portion 26 is available for deformation, and the greater the deformation resistance becomes. It can be appreciated that the different forces required for venous insertion and removal of the electrode tip 12 due to the configuration of the tines 20 and the restraining wedge 22 as explained above will also result in one force being required for insertion and location of the electrode tip 12 with respect to the heart trabeculae, and a greater force required to disengage the electrode tip 12 and tines 20 from the heart trabeculae.

In operation, as the tines 20 are bent away from the electrode tip 12, the force required to push the electrode tip 12 into the trabeculae tends to be minimized. However, once positioned, the restraining wedge 22 tends to restrict forward movement of the tines 20 towards the electrode tip 12 thereby increasing the force required to disengage the electrode tip 12 from the trabeculae. As previously explained, selecting the height of the blocking surface 25 with respect to the tine 20 length, and the diameter of the non-weakened portion 26, the amount of force required to disengage the tines 20 from the trabeculae can be predetermined while still maintaining the same amount of force required for venous insertion of the electrode as determined by the diameter of the weakened portion 24. By varying these two parameters during manufacture, a substantially independent means is provided for adjusting the force required to insert the lead with respect to the force required to remove the lead. As soon as the electrode tip 12 has been moved forward sufficiently so that the end of the tines 20 extend beyond one or more of the trabeculae, they will tend to spring out to their ninety degree undeformed position, thereby tending to hold the electrode tip 12 in position. Once extended, they will no longer tend to push the electrode tip 12 out of position, thereby maintaining contact between the electrode tip 12 and the heart.

Although the exemplary embodiment has utilized a rounded tine and a truncated cone for the restraining wedge 22, it should be recognized that other stop means and tine configurations could be utilized. For example, an alternate configuration of the stop means can be seen in FIGS. 10 and 11. Tines 20', encasing tube 16', and electrode tip 12' are provided as in the preceding embodiment. However, instead of the conically-shaped restraining wedge 22 shown in FIG. 3, four upwardly protruding restraining wedges 40 are utilized. Each of the restraining wedges 40 are positioned between a tine 20' and the electrode tip 12' so that a restraining wedge blocking surface 42 is positioned directly between its corresponding tine 20' and the electrode tip 12'. One advantage of this embodiment is that the tines 20' and restraining wedges 40 can be formed as one piece and then separated along blocking surface 42 by an appropriate cutting tool. It should be noted that the withdrawal force can also be decreased by spacing apart the blocking surface 42 from the tine 20', thereby allowing some deformation of the entire tine 20' to occur before it abuts against the blocking surface 42.

A further embodiment of the invention can be seen in FIG. 12. Here, a tine 50 protrudes from the encasing material 52. An electrode tip 54 is attached to a central electrical conductor (not shown) which is centrally positioned in the encasing material 52. A slit 56 is formed in the encasing material beginning at the tine-/encasing material interface point that is proximal to said electrode tip 54. The slit 56 forms an acute angle A with respect to a line 60 which extends from the electrode tip 54 along the longitudinal axis of the central conductor. It should be noted that the embodiment of FIG. 12 shows the slit 56 forming an acute angle A with respect to the line 60. However, angle A need not necessarily be acute but rather need only be such that the effective cross-sectional thickness of the tine is reduced as it is folded back and away from the electrode tip 54 with respect to the effective cross-sectional thickness as it is moved towards the electrode tip 54.

A further embodiment of the invention is shown in FIG. 13. Here, nonconducting encasing material 70 surrounds a central conductor 72 which is attached to an electrode tip 74. Tines 76 are formed at the end of the encasing material 70 and located so that one surface abuts against the inner surface 78 of the electrode tip 74. A weakened portion 80 similar to that shown in FIG. 3 embodiment is also provided. In operation, the tine 76 abuts against the electrode surface 78 when its tip is moved towards the electrode tip 74, thus creating a first deformation resistance. A second deformation resistance lower than the first deformation resistence is provided when the tine tip is moved away from the electrode tip 74, this lower resistence being partially due to the weakened portion 80.

I claim:

1. In an endocardial electrode of the type having an electrical conductor encased in an encasing material which is generally inert to body fluids, the conductor terminating at an exposed electrically conductive electrode tip, the improvement comprising:

resilient tine means near the electrode tip comprising at least one tine for cooperating with heart tissue and holding the electrode tip in position, said tine exhibiting a first deformation resistance when said tine tip is moved away from the electrode tip, and means for blocking the movement of a portion of said tine as said tine tip is moved towards the electrode tip, thereby providing a second deformation resistance which is greater than said first deformation resistance.

2. The improvement of claim 1 wherein said tine when unrestrained forms a substantially ninety degree angle with respect to the electrical conductor.

3. The improvement of claim 1 or 2 wherein said means for blocking comprises stop means for abutting against a portion of said tine surface facing the electrode tip, thereby increasing the deformation resistance when said tine tip is moved towards the electrode tip.

4. The improvement of claim 3 wherein said stop means defines a surface substantially orthogonal to, and symetrical about, the electrical conductor, said surface extending from the encasing material to a predetermined distance from said tine tip.

5. The improvement of claim 4 wherein said stop means is formed as a truncated cone symetrically positioned about the electrical conductor, said cone being formed of a nonconductive material which is generally inert to body fluids.

6. The improvement of claim 5 wherein said cone surface tapers towards the electrode tip.

7. The improvement of claim 4 wherein said stop means is defined by a portion of the electrode tip.

8. The improvement of claim 3 wherein said tine is configured to have a weakened portion proximal to the base of said tine.

9. The imporvement of claim 8 wherein said weakened portion has a smaller thickness than another portion of said tine distal from said tine base.

10. The improvement of claim 9 wherein said smaller cross-sectional area is offset with respect to the centerline of said tine.

11. The improvement of claim 3 wherein said stop means comprises a wedge-shaped protrusion extending from the encasing material and defining a surface extending from the encasing material to a predetermined distance from said tine tip.

12. The improvement of claim 11 wherein said surface defined by said stop means is substantially orthogonal to the electrical conductor.

13. The improvement of claim 1 wherein said tine means comprises four tines.

14. In an endocardial electrode of the type having an electrical conductor encased in an encasing material which is generally inert to body fluids, the conductor terminating at an exposed electrically conductive electrode tip, the improvement comprising:

resilient tine means near the electrode tip comprising at least one tine for cooperating with heart tissue and holding the electrode tip is position, said tine exhibiting a first deformation resistance when said tine tip is moved away from the electrode tip; and means for providing a second deformation resistance when said tine tip is moved towards the electrode tip, said means for providing comprising said encasing material being formed to define a slit extending downwardly into said encasing material adjacent to the location where said tine intersects said encasing material.

15. The improvement of claim 14 wherein said location at which said tine intersects said encasing material is proximal to said electrode tip, said slit surfaces forming an acute angle with respect to a line extending between said electrode tip and said tine along the longitudinal axis of said electrical conductor.

16. In an endocardial electrode of the type having an electrical conductor encased in an encasing material which is generally inert to body fluids, the conductor terminating at an exposed electrically conductive electrode tip, the improvement comprising:

tine means near the electrode tip and comprising at least one tine for cooperating with heart tissue and holding the electrode tip in position, said tine when unrestrained forming a substantially ninety degree angle with respect to the electrical conductor and being of a pliant material having sufficient rigidity to maintain said ninety degree angle when unrestrained, but sufficiently pliant to prevent penetration of said heart tissue, said pliant material being generally inert to body fluids, said tine exhibiting a first deformation resistance when its tip is moved away from the electrode tip; and means for providing a second deformation resistance greater than said first deformation resistance when said tine tip is moved towards the electrode tip.

17. The improvement of claim 16 wherein said means for providing comprises stop means for allowing only a first predetermined portion of said tine including said tine tip to bend towards the electrode tip.

18. The improvement of claim 17 wherein the cross-sectional area of a portion of said tine within said first predetermined portion is greater than the cross-sectional area of a portion of said tine not within said first predetermined portion.

19. The improvement of claim 17 wherein said stop means defines a surface adjacent to said tine for allowing only said first predetermined portion to bend towards the electrode tip.

20. The improvement of claim 17 wherein said stop means comprises a portion of the electrode tip.

21. The improvement of claim 17 wherein said stop means comprises a wedge-shaped protrusion extending outwardly from the encasing material and defining a surface substantially orthogonal to the electrical conductor, said surface being adjacent to a portion of said tine facing the electrode tip and extending to a predetermined distance from said tine tip.

22. The improvement of claim 16 wherein said means for providing said second deformation resistance comprises said encasing materials being formed to define a slit which intersects said encasing material, said slit extending downwardly into said encasing material and being located so as to create a greater resistance to bending of the tine in the direction of the electrode tip than away from the electrode tip.

23. The improvement of claim 22 wherein a point at which said tine intersects said encasing material is proximal to said electrode tip, said slit surfaces forming an acute angle with respect to a line extending from said electrode tip along the longitudinal axis of said electrical conductor.

* * * * *